(12) United States Patent
Dezard et al.

(10) Patent No.: US 10,144,705 B2
(45) Date of Patent: Dec. 4, 2018

(54) METHOD FOR PREPARING CREATINE FATTY ESTERS, CREATINE FATTY ESTERS THUS PREPARED AND USES THEREOF

(71) Applicant: Commissariat a l'energie atomique et aux energies alternatives, Paris (FR)

(72) Inventors: Sophie Dezard, Forges-les-Bains (FR); Frederic Taran, Gif sur Yvette (FR); Alexandra Trotier-Faurion, Bourg la Reine (FR); Aloise Mabondzo, Paris (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/418,418

(22) PCT Filed: Jul. 17, 2013

(86) PCT No.: PCT/EP2013/065109
§ 371 (c)(1),
(2) Date: Jan. 29, 2015

(87) PCT Pub. No.: WO2014/019855
PCT Pub. Date: Feb. 6, 2014

(65) Prior Publication Data
US 2015/0299112 A1    Oct. 22, 2015

(30) Foreign Application Priority Data
Jul. 30, 2012 (EP) .................................. 12352002

(51) Int. Cl.
| | | |
|---|---|---|
| *C07C 279/14* | (2006.01) | |
| *C07C 277/08* | (2006.01) | |
| *C07C 233/88* | (2006.01) | |
| *A23L 33/175* | (2016.01) | |
| *C07D 233/88* | (2006.01) | |

(52) U.S. Cl.
CPC .......... *C07C 279/14* (2013.01); *A23L 33/175* (2016.08); *C07C 277/08* (2013.01); *C07D 233/88* (2013.01); *A23V 2002/00* (2013.01)

(58) Field of Classification Search
CPC ........................... C07C 279/14; C07D 233/88
See application file for complete search history.

(56) References Cited

U.S. PATENT DOCUMENTS

| | | |
|---|---|---|
| 6,413,552 B1 | 7/2002 | Stoll |
| 2002/0049253 A1 | 4/2002 | Kaddurah-Daouk |
| 2003/0212130 A1 | 11/2003 | Miller et al. |
| 2005/0049428 A1 | 3/2005 | Vennerstrom |
| 2008/0200705 A1 | 8/2008 | Chaudhuri et al. |
| 2011/0269986 A1 | 11/2011 | Burov et al. |

FOREIGN PATENT DOCUMENTS

| | | |
|---|---|---|
| CN | 1616420 | 5/2005 |
| CN | 1900056 | 1/2007 |
| WO | WO 02/22135 A1 | 3/2002 |
| WO | WO 2008/101309 A1 | 8/2008 |

OTHER PUBLICATIONS

McDermid, www.news-Medical.net, Creatine Monohydrate disappoints in Parkinson's disease, 2015, recovered from http://www.newsmedical.net/news/20150213/Creatine-monohydrate-disappoints-in-Parkinsone28099s-disease.aspx on Aug. 2, 2016, pp. 1-3.*
Dox et al, The Journal of Biological Chemistry, Esterification of Creatine, 1922, 54, pp. 671-673.*
Edgar et al.,Journal of the American Chemical Society, The equilibrium between creatine and creatinine, in aqueous solution. The effects of hydrogen ion., 1925, 47, pp. 1179-1188.*
Solomons , Organic Chemistry, 5th Edition, 1992, John Wiley & Sons, New York, pp. 976-978.*
Wild, HDBuzz, Largest creatine clinical trial for Huntington's Disease halted after 'futility' analysis, 2014, pp. 1-4, recovered from https://en.hdbuzz.net/181 on Dec. 13, 2017. (Year: 2014).*
Rosenfeld et al, Amyotrophic Lateral Sclerosis, Creatine Monohydrate in ALS: Effects on strength, fatigue, respiratory status and ALSFRS, 2008, 9, pp. 26-272. (Year: 2008)*
Allen, Neuroscience Biobehavior Reviews, Creatine metabolism and psychiatric disorders: Does creatine supplementation have therapeutic value?, 2012, 36(5), pp. 1442-1462. (Year: 2012).*
International Search Report dated Aug. 29, 2013 for International Patent Application No. PCT/EP2013/065109.
European Search Report dated Nov. 14, 2012 for European Patent Application No. 12 35 2002.
Edgar et al., "The equilibrium between creatine and creatinine, in aqueous solution. The effects of hydrogen ion". J. Amer. Chem. Soc., vol. 47, pp. 1179-1188 (Apr. 1925).
Gers et al., "Reagents for efficient conversion of amines to protected guanidines", Synthesis, vol. 2004, pp. 37-42 (Sep. 2003).
Robles et al., "Towards nucleopeptides containing any trifunctional amino acid", Tetrahedron, vol. 55, pp. 13251-13261 (1999).

* cited by examiner

*Primary Examiner* — Paul A Zucker
(74) *Attorney, Agent, or Firm* — Miles & Stockbridge P.C.

(57) ABSTRACT

The present invention concerns a method for preparing a creatine fatty ester or derivative thereof comprising at least one step consisting in reacting a diprotected creatinine with a molecule bearing at least one alcohol functional group and of formula R'—OH in which R' represents a hydrocarbon radical containing at least 4 carbon atoms. The present invention also concerns particular creatine fatty esters or derivative thereof and medical uses thereof.

21 Claims, 5 Drawing Sheets

Scheme 1

Figure 1:
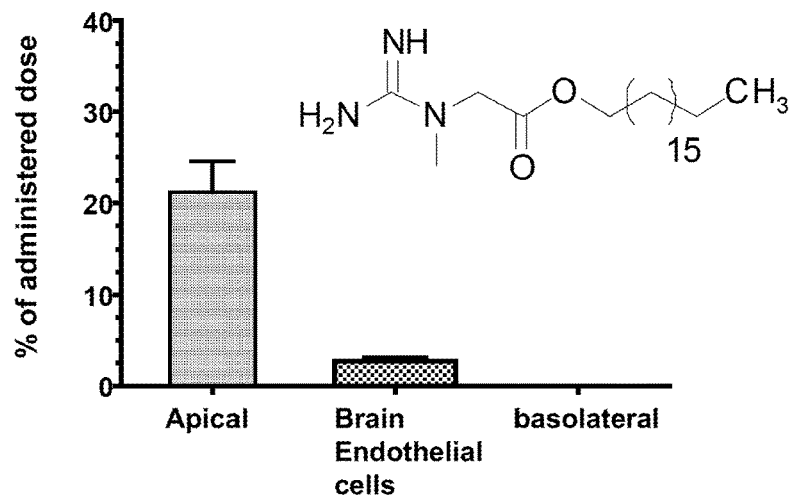

METHOD FOR PREPARING CREATINE FATTY ESTERS, CREATINE FATTY ESTERS THUS PREPARED AND USES THEREOF

TECHNICAL FIELD

The present invention belongs to the domain of creatine derivatives and notably to creatine fatty esters.

More particularly, the present invention relates to a method for preparing (or producing) creatine fatty esters by carrying out a ring opening step on diprotected creatinine using a molecule bearing an alcohol functional group.

The present invention also concerns particular creatine fatty esters thus prepared and the different uses of these new creatine fatty esters in research, therapy, imaging or diagnosis.

STATE OF THE PRIOR ART

Creatine is an endogenous nutrient produced naturally by the liver and kidneys in most vertebrates. The uses of creatine are many, including use as supplement to increase muscle mass and enhance muscle performance as well as in emerging applications in the treatment of various disorders such as, without limitation, Parkinson's disease, Huntington's disease, various neuromuscular disorders, hypoxia and ischemic brain diseases such as stroke, heart disease, various muscular dystrophies [1] and various skin disorders [2]. Creatine may also be used as anti-inflammatory agent [3]. Notably, local administration of creatine can be achieved by absorption through the skin [4].

Typically, creatine is taken up into muscle cells by specific receptors and converted to phosphocreatine by creatine kinase. Muscle cells, including skeletal muscle and the heart muscle, function by utilizing cellular energy released from the conversion of adenosine triphosphate (ATP) to adenosine diphosphate (ADP). The amount of phosphocreatine in the muscle cell determines the amount of time it will take for the muscle to recover from activity and regenerate ATP. Phosphocreatine is a rapidly accessible source of phosphate required for regeneration of ATP and sustained use of the muscle. For example, energy used to expand and contract muscles is supplied by ATP. ATP is metabolized in the muscle by cleaving a phosphate radical to release energy needed to contract the muscle. Adenosine diphosphate (ADP) is formed as a byproduct of this metabolism.

The most common sources of ATP are from glycogen and creatine phosphate. Creatine phosphate is favored as a ready source of phosphate because it is able to resynthetize ATP at a greater rate than is typically achieved utilizing glycogen. Therefore, increasing the amount of creatine in the muscle increases the muscle stores of phosphocreatine and has been proven to increase muscle performance and increase muscle mass.

However, creatine itself is poorly soluble in an aqueous solution (about 10-15 mg/ml). Further creatine is not well absorbed from the gastrointestinal (GI) tract. Indeed, creatine has been estimated to have a 14% or less absorption rate from the GI tract. Creatine also has low oral bioavailability due, in part, to (i) low lipophilicity and therefore poor membrane permeability, and (ii) rapid conversion to creatinine in the acidic environment of the stomach [5]. Thus, current products require administration of large amounts, typically 5 grams or more, of creatine in order to be effective, which causes side effects as bloating, gastrointestinal (GI) distress, diarrhea, and the like.

The deficits of the metabolism of creatine, include enzymatic deficits of its biosynthesis (deficits in AGAT and GAMT of recessive autosomic transmission) and of its intra-cerebral transport (gene SLC6A8/CT1, related to X). The incidence of the disease is approximately 2% of all X-linked mental retardation of unknown ethiology. These deficits result in severe backwardnesses with a prevalence on the language, an extrapyramidal syndrome, disorders of behavior and in certain cases epilepsy. The disease appears most of the time during childhood but adult cases were recently reported.

The response to a treatment by creatine seems to be favorable only in the case of a deficit in the synthesis of creatine but not in the case of a deficit of intra-cerebral transport of creatine. Indeed, in this case, the findings of the two years of treatment creatine by oral administration associated with its precursors L-Arginine and L-Glycine showed neither real improvement nor an increase in intra-cerebral creatine levels. Thus this is a clinical situation where the absence of functional transporters of creatine at the blood-brain barrier (BBB) prevents the entry of creatine in the brain affecting the cerebral functions. A better definition and an evaluation of new strategies for pharmacological optimization for this cerebral metabolic disease are thus today more than necessary.

These diseases and the above-described shortcomings and side effects can be avoided by the administration of creatine esters, which are converted into creatine by endogenous esterases found in a variety of cells and biological fluids [1]. Creatine esters are more lipophilic than creatine and therefore have a greater bioavailability. Additionally, the carboxylic acid functional group of creatine is masked through esterification in creatine esters, thereby preventing the formation of the undesired product creatinine.

All creatine fatty esters methods described in patents and patent applications involve Brönsted acids-catalyzed reaction of creatine with alcohols. Creatine esters can be formed by reaction of creatine with alcohols by gaseous hydrochloride catalysis [6]. Creatine fatty esters can also be formed from direct synthesis by in situ acid production of an acid catalyst [7-8]. The patent application [7] discloses several creatine esters obtainable by this synthesis (paragraph [0022]). In these creatine esters, the hydrocarbyl group substituting the oxygen atom of the ester function can comprise from 1 to 25 carbon atom(s).

Other creatine derivatives are disclosed in the prior art. Creatine fatty acid anhydrides are prepared by direct reaction of creatine with fatty acyl halide [9]. Creatinyl amides are produced by guanidinylation of sarcosine peptide to produce creatinyl aminoacids [10]. Amide linkage between the guanidyl group of creatinine and fatty acid is also described [11]. Nevertheless, in the inventors' hands, the preparation of fatty esters as fatty anhydrides according to these patents and patent applications gave very poor yields. These methods are well adapted to alcohols of low molecular weight such as EtOH, nPrOH and nBuOH but yields are dramatically reduced in case of fatty, long chain alcohols.

Clearly, a need exists for a process allowing efficient production of creatine fatty esters. Indeed, an efficient synthesis of creatine fatty esters would be a significant progress in the therapeutic and diagnostic fields.

DISCUSSION OF THE INVENTION

The present invention solves the above-listed technical problems and provides a solution to the aforementioned need. Indeed, the inventors describe the production of creatine fatty esters using fatty alcohols with an overall yield of 45%. The efficiency of this process is higher than those previously described in literature and allows obtaining creatine derivatives that are difficult to prepare by known techniques.

In addition, the synthesis according to the present invention is cheap and can be applied at the multi-gram scale for therapeutic needs.

Then, the preparation method according to the present invention can be carried by any fatty alcohol, but also by any molecule bearing at least one alcohol functional group such as, for example, glucose.

More particularly, the present invention concerns a method for preparing a creatine fatty ester or derivative thereof comprising at least one step consisting in reacting a diprotected creatinine with a molecule bearing at least one alcohol functional group and of formula (I):

in which R' represents a hydrocarbon radical containing at least 4 carbon atoms.

In what precedes and what follows, creatine (2-1(methylguanidino) acetic acid) is represented by the following formula (II):

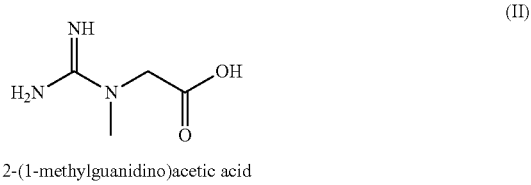

2-(1-methylguanidino)acetic acid

Creatine can also be represented by the following formula (II'):

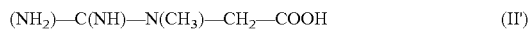

In the present invention, a creatine fatty ester is represented by the formula (III):

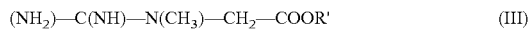

in which R' represents a hydrocarbon radical containing at least 4 carbon atoms.

In the present invention, a creatine fatty ester derivative is a creatine fatty ester in which at least one of the hydrogen atoms of the methylguanidinyl group is substituted by a carboxylic acid group (—COOH). Advantageously, the creatine derivative is represented by the following formula (IV):

in which the radical R' represents a hydrocarbon radical containing at least 4 carbon atoms and the radicals $R_1$, $R_2$ and $R_3$, identical or different, represent an hydrogen atom or a carboxylic acid group and at least one among the radicals $R_1$, $R_2$ and $R_3$ is a carboxylic acid group.

Particularly, in the creatine derivative represented by the formula (IV), only one radical among $R_1$, $R_2$ and $R_3$ is a carboxylic acid group and the two other radicals are hydrogen atoms. More particularly, the radical $R_1$ is a carboxylic acid group and the radicals $R_2$ and $R_3$ are hydrogen atoms. In this case, the creatine derivative is of the following formula (V):

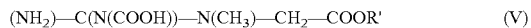

in which the radical R' represents a hydrocarbon radical containing at least 4 carbon atoms.

In what precedes and what follows, creatinine (2-imino-1 methylimidazolidin-4-one) is represented by the following formula (VI):

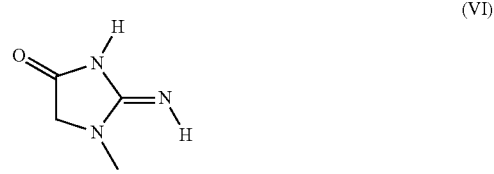

2-imino-1-methylimidazolidin-4-one

In the present invention, diprotected creatinine is a creatinine in which the two hydrogen atoms substituting the two nitrogen atoms are replaced by two protecting groups, identical or different. It is clear that the protection is not borne by the methyl group substituting the $3^{rd}$ nitrogen atom of the creatinine. In a diprotected creatinine, the two protecting groups are advantageously identical.

Any adapted protecting group known by one of ordinary skill in the art can be used in the context of the present invention.

Advantageously, the protecting group implemented in the present invention is represented by the formula (VII):

in which the radical $R_4$ represents a hydrocarbon group.

The hydrocarbon group $R_4$ is a hydrocarbon group with 1 to 20 carbon atoms such as an alkyl radical with 1 to 20 carbon atoms, an alkenyl radical with 2 to 20 carbon atoms, an alkoxy radical with 1 to 20 carbon atoms, an aryl radical with 6 to 20 carbon atoms, and an aryloxy radical with 6 to 20 carbon atoms.

Within the scope of the present invention and unless indicated otherwise, by «alkyl group with 1 to 20 carbon atoms» is meant a linear, branched or cyclic (hetero)alkyl group, optionally substituted, with 1 to 20 carbon atoms, notably with 1 to 15 carbon atoms and in particular, with 1 to 10 carbon atoms, the heteroatom(s) of the heteroalkyl group being N, O, P or S.

Within the scope of the present invention, by «alkenyl group with 2 to 20 carbon atoms» is meant a linear, branched or cyclic (hetero)alkenyl group, optionally substituted, with 2 to 20 carbon atoms, notably with 2 to 15 carbon atoms and in particular, with 2 to 10 carbon atoms, the heteroatom(s) of the heteroalkenyl group being N, O, P or S.

Within the scope of the present invention, by «alkoxy group with 1 to 20 carbon atoms» is meant an oxygen atom substituted with an alkyl with 1 to 20 carbon atoms as defined earlier.

Within the scope of the present invention, by «aryl group with 6 to 20 carbon atoms», is meant a mono- or poly-cyclic (hetero)aromatic group, optionally substituted, having from 6 to 20 carbon atoms, notably from 6 to 14 carbon atoms, in particular, from 6 to 8 carbon atoms, the heteroatom(s) of the heteroaromatic group being N, O, P or S.

Within the scope of the present invention, by «aryloxy group with 6 to 20 carbon atoms» is meant an oxygen atom substituted with an aryl with 6 to 20 carbon atoms as defined earlier.

Within the scope of the present invention, by «optionally substituted» is meant a radical which can be substituted with one or more groups selected from an alkyl group, an aryl group, an alkoxy group, a halogen, a hydroxy, a cyano, a trifluoromethyl or a nitro.

Within the scope of the present invention, by «halogen» is meant a fluorine, chlorine, bromine or iodine.

Particularly, the protecting group $R_4$ implemented in the present invention is chosen from the group consisting of an optionally substituted benzoyl group, a tert-butoxycarbonyl (BOC) group and a fluorenylmethoxy carbonyl (FMOC) group. More particularly, the protecting group implemented in the present invention is an optionally substituted benzoyl group and notably a benzoyl group.

The radical R' present in the molecule bearing at least one alcohol functional group and of formula (I), in the creatine fatty ester of formula (III) and in the creatine fatty ester derivative of formula (IV) or (V) is a hydrocarbon radical containing at least 4 carbon atoms. Advantageously, the radical R' is chosen in the group consisting of an alkyl radical with 4 to 30 carbon atoms, an alkenyl radical with 4 to 30 carbon atoms, and an aryl radical with 6 to 30 carbon atoms.

Within the scope of the present invention and unless indicated otherwise, by «alkyl group with 4 to 30 carbon atoms» is meant a linear, branched or cyclic (hetero)alkyl group, optionally substituted, with 4 to 30 carbon atoms, notably with 4 to 25 carbon atoms and in particular, with 4 to 20 carbon atoms, the heteroatom(s) of the heteroalkyl group being N, O, P or S.

Within the scope of the present invention, by «alkenyl group with 4 to 30 carbon atoms» is meant a linear, branched or cyclic (hetero)alkenyl group, optionally substituted, with 4 to 30 carbon atoms, notably with 4 to 25 carbon atoms and in particular, with 4 to 20 carbon atoms, the heteroatom(s) of the heteroalkenyl group being N, O, P or S.

Within the scope of the present invention, by «aryl group with 6 to 30 carbon atoms», is meant a mono- or poly-cyclic (hetero)aromatic group, optionally substituted, having from 6 to 30 carbon atoms, notably from 6 to 25 carbon atoms, in particular, from 6 to 20 carbon atoms, the heteroatom(s) of the heteroaromatic group being N, O, P or S.

In a 1$^{st}$ particular embodiment of the present invention, the radical R' present in the molecule bearing at least one alcohol functional group and of formula (I), in the creatine fatty ester of formula (III) and in the creatine fatty ester derivative of formula (IV) or (V) is represented by the following formula (VIII):

—CH$_2$—R'$_1$ (VIII)

in which R'$_1$ is a hydrocarbon radical containing at least 3 carbon atoms. Advantageously, the radical R'$_1$ is chosen in the group consisting of an alkyl radical with 3 to 30 carbon atoms, an alkenyl radical with 3 to 30 carbon atoms, and an aryl radical with 6 to 30 carbon atoms.

Within the scope of the present invention and unless indicated otherwise, by «alkyl group with 3 to 30 carbon atoms» is meant a linear, branched or cyclic (hetero)alkyl group, optionally substituted, with 3 to 30 carbon atoms, notably with 3 to 25 carbon atoms and in particular, with 3 to 20 carbon atoms, the heteroatom(s) of the heteroalkyl group being N, O, P or S.

Within the scope of the present invention, by «alkenyl group with 3 to 30 carbon atoms» is meant a linear, branched or cyclic (hetero)alkenyl group, optionally substituted, with 3 to 30 carbon atoms, notably with 3 to 25 carbon atoms and in particular, with 3 to 20 carbon atoms, the heteroatom(s) of the heteroalkenyl group being N, O, P or S.

In a 2$^{nd}$ particular embodiment of the present invention, the radical R' present in the molecule bearing at least one alcohol functional group and of formula (I), in the creatine fatty ester of formula (III) and in the creatine fatty ester derivative of formula (IV) or (V) is a glucosyl radical optionally substituted.

In what follows, glucose can be represented by the following Fischer formula (IX):

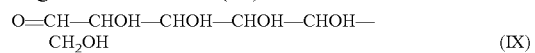

Alternatively, glucose can be represented by the formula (X):

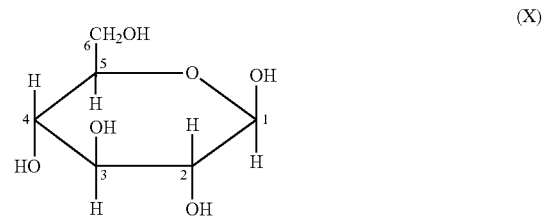

By «glucosyl radical», is meant a radical of formula $C_6H_{11}O_5$ derived from glucose by elimination of one of the hydroxyl group thereof. The eliminated hydroxyl group can be borne by one of the 5 carbon atoms $C_1$, $C_2$, $C_3$, $C_4$ or $C_6$ (carbon nomenclature refers to formula (X)).

By «substituted glucosyl radical», is meant a glucosyl radical substituted with one or more substitution groups selected from an alkyl group, an aryl group, an alkoxy group, a halogen, a cyano, a trifluoromethyl or a nitro.

In a 1$^{st}$ embodiment, the eliminated hydroxyl group is the one of the carbon atom $C_6$ and thus the glucosyl radical can be represented by the following formula (XI):

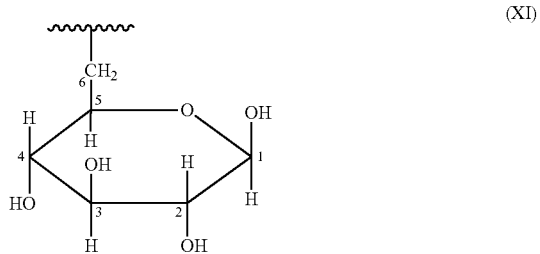

In this 1$^{st}$ embodiment, a substituted glucosyl radical can be represented by the following formula (XII):

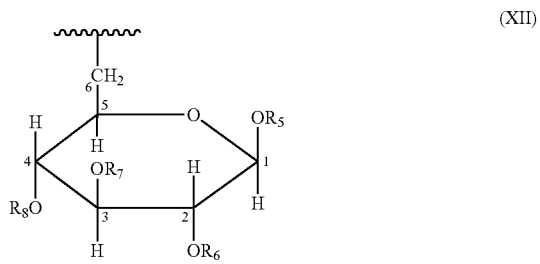

in which the radicals $R_5$, $R_6$, $R_7$ and $R_8$, identical or different, represent a substitution group as previously defined.

Advantageously, the radicals $R_5$, $R_6$, $R_7$ and $R_8$ are identical groups and notably each represents a benzyl group.

Alternatively, the radicals $R_5$, $R_6$, $R_7$ and $R_8$ represent each a group selected from an alkyl group such as a methyl group or an ethyl group and an aryl group such as a benzyl group. In particular, the radical $R_5$ is a methyl group and the radicals $R_6$, $R_7$ and $R_8$ are benzyl groups.

In a $2^{nd}$ embodiment, the eliminated hydroxyl group is the one of the carbon atom $C_1$ and thus the glucosyl radical can be represented by the following formula (XIII):

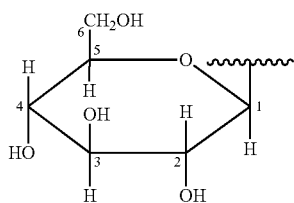

(XIII)

In this $2^{nd}$ embodiment, a substituted glucosyl radical can be represented by the following formula (XIV):

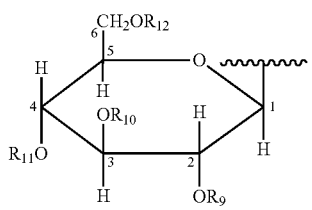

(XIV)

in which the radicals $R_9$, $R_{10}$, $R_{11}$ and $R_{12}$, identical or different, represent a substitution group as previously defined.

Advantageously, the radicals $R_9$, $R_{10}$, $R_{11}$ and $R_{12}$ are identical groups and notably each represents a benzyl group.

Alternatively, the radicals $R_9$, $R_{10}$, $R_{11}$ and $R_{12}$ represent each a group selected from an alkyl group such as a methyl group or an ethyl group and an aryl group such as a benzyl group.

In the present invention, the compounds of formulae (I), (II), (II'), (III), (IV), (V), (VI), (VII), (VIII), (IX), (X), (XI), (XII), (XIII) and (XIV) can present one or more radioisotope(s), advantageously chosen from iodine-123, iodine-125, iodine-126, iodine-133, iodine-131, iodine-124, indium-111, indium-113m, bromine-77, bromine-76, gallium-67, gallium-68, ruthenium-95, ruthenium-97, technetium-99m, fluorine-19, fluorine-18, carbon-13, carbon-11, nitrogen-15, nitrogen-13, oxygen-17, oxygen-15, oxygen-14, scandium-47, tellurium-122m, thulium-165, yttrium-199, copper-64, copper-62, gadolidium-68 and rubidium-82.

Advantageously, the preparation method of a creatine fatty ester or derivative thereof according to the present invention comprises the following successive steps consisting in:

a) reacting creatinine with a protective agent to obtain a diprotected creatinine, as defined earlier;

b) reacting the diprotected creatinine obtained at step (a) with a molecule bearing at least one alcohol functional group and of formula (I) as defined earlier to obtain a diprotected creatine fatty ester; and c) deprotecting the diprotected creatine fatty ester or derivative thereof obtained at step (b), in order to obtain said creatine fatty ester or derivative thereof as defined earlier.

Step (a) of the preparation method according to the present invention consists in protecting the guanidine group of creatinine.

This protection can be carried out by any protection method known by one of ordinary skill in the art. The latter will know, as a function of the protecting groups to be introduced in creatinine, how to choose the most appropriate protective agent and experimental conditions.

As already explained, the groups protecting the guanidine group of creatinine are advantageously of formula (VI). In these conditions, step (a) consists in putting into contact the creatinine with a protective agent capable of producing a protecting group as previously defined, to obtain a diprotected creatinine. Advantageously, such protective agent is of formula (XV):

$$Cl\text{—}C(O)\text{—}OR_4 \qquad (XV)$$

in which the radical $R_4$ represents a hydrocarbon group, as previously defined.

Step (a) can be carried out by any protection method known by one of ordinary skill in the art. The latter will know, as a function of the protective agent that is employed, how to choose the most appropriate method of protection.

For example, when such protective agent is of formula (XV), the solvent in the solution containing creatinine and this protective agent is typically dichloromethane (DCM) and notably anhydrous DCM. This solution can also contain any chemical compound which might facilitate the formation of diprotected creatinine. For example, such facilitating chemical compound can be the Hünig's base or N,N-diisopropyl ethylamine (DIEPA). For one equivalent of creatinine, the solution implemented can contain between 1, 5 and 7 equivalents and notably between 2 and 4 equivalents of protective agent. Similarly, for one equivalent of creatinine, the solution implemented can contain between 1, 5 and 7 equivalents and notably between 2 and 4 equivalents of DIEPA. Advantageously, the amount of protective agent and of DIEPA expressed in equivalents is identical in the implemented solution.

Step (a) can be performed under inert atmosphere and, for example, under nitrogen.

The solution implemented during the step (a) of the method according to the present invention can be subject to stirring for creatinine and protective agent to react together. Any mechanical technique allowing stirring may be used for this purpose. As examples of such techniques, manual stirring, treatment with ultrasounds, mechanical stirring or a combination of such techniques may be mentioned. These techniques may require the use of a magnetic stirrer and of a magnetized bar or an ultrasonic bath or of a mechanical stirrer with rods, vanes, propellers, etc. This stirring may last for 1 min to 1 h, notably from 15 to 45 min at a temperature comprised between 0 and 10° C., notably between 2 and 6° C. and continue between 6 and 18 h, notably between 10 and 15 h at a temperature comprised between 8 and 40° C., notably 12 and 30° C. and, particularly, at room temperature (RT) (i.e. 20° C.±4° C.).

The diprotected creatinine obtained after step (a) is easily purified. Indeed, once the step (a) of the method according to the present invention achieved, the diprotected creatinine thus obtained can be purified prior to step (b) by any purification technique known by one having ordinary skill in the art. By way of non-limiting examples, mention may be made of chromatography, flash chromatography, flash chromatography on silica gel and notably on silica gel with Heptane/Ethyl Acetate gradient, a semi-preparative HPLC, etc.

In the method of the present invention, step (b) consists in producing a diprotected creatine fatty ester, which is performed by reacting the diprotected creatinine with the molecule bearing at least one alcohol functional group and of formula (I) as defined earlier. The reaction consists in a nucleophilic addition of the molecule of formula (I) on the diprotected creatinine.

In a particular embodiment, the solvent solution implemented during step (b) is the molecule bearing at least one alcohol functional group and of formula (I). One can say that the step (b) is performed without solvent, which means without any other solvent than the molecule bearing at least one alcohol functional group and of formula (I).

Alternatively, an additional solvent can be added to the solution containing the diprotected creatinine and the molecule bearing at least one alcohol functional group and of formula (I). As for example of additional solvent usable, one can cite toluene.

In the solution implemented at step (b), for one equivalent of diprotected creatinine, the amount of molecule bearing at least one alcohol functional group and of formula (I) expressed in equivalent is comprised between 1 and 15, notably between 1 and 10. The table 5 hereinafter presents different molecules bearing at least one alcohol functional group and of formula (I) and the amount thereof used at step (b) of the present invention.

The step (b) is carried out during 1 to 20 h, notably during 2 to 16 h, and particularly, during 2 to 10 h. Typically, it can be carried out during about 3 h (i.e. 3 h±30 min), about 4 h (i.e. 4 h±30 min), about 5 h (i.e. 5 h±30 min) or about 6 h (i.e. 6 h±1 h). This step (b) is carried out under atmospheric pressure and at a temperature comprised between 60 and 100° C., notably 70 and 90° C. and, particularly, at around 80° C. (i.e. 80° C.±5° C.).

Once the step (b) of the method according to the present invention achieved, the diprotected creatine ester thus obtained can be purified prior to step (b) by any purification technique known by one having ordinary skill in the art. By way of non-limiting examples, mention may be made of chromatography, flash chromatography, flash chromatography on silica gel and notably on silica gel with Heptane/Ethyl Acetate gradient, a semi-preparative HPLC, etc.

The structure and purity of diprotected creatine fatty ester is determined after purification on silica gel by Liquid Chromatography-Mass Spectrometry (LC/MS), Thin Layer Chromatography (TLC), Nuclear Magnetic Resonance (NMR) and, in particular, $^1$H-NMR and $^{13}$C-NMR, InfraRed spectroscopy (IR spectroscopy) and/or melting point determination.

The deprotection step (c) is carried out for passing from the diprotected creatine fatty ester obtained in step (b) to the creatine fatty ester of formula (III) or to the creatine fatty ester derivative of formula (IV) or (V).

The elimination of the protecting groups of the amine functions of the diprotected creatine fatty ester, i.e. the deprotection, can be carried out by any deprotection method known by one of ordinary skill in the art. The latter will know, as a function of the protecting groups that are employed, how to choose the most appropriate method of deprotection.

Advantageously, when the protecting group is a compound of formula (VII), step (c) is achieved by hydrogen in the presence of supported palladium over alumina or charcoal. This reaction is carried out in a solvent advantageously selected from dichloroethane (DCE), dichloromethane (DCM), acetonitrile (CH$_3$CN) or a mixture of DCM and a lower alcohol. By "lower alcohol" is meant in the context of the present invention an aliphatic alcohol having 1 to 3 carbon atoms, such as methanol, ethanol and propanol. More particularly, the mixture of DCM/lower alcohol used as solvent in deprotection step (c) is a DCM/methanol mixture.

This deprotection step (c) is carried out during 1 to 6 h, notably during 2 to 4 h and, particularly, during about 3 h (i.e. 3 h±30 min). This deprotection step (c) is also carried out under atmospheric pressure and at a temperature comprised between 8 and 40° C., notably 12 and 30° C. and, particularly, at room temperature (RT) (i.e. 20° C.±4° C.).

In a particular embodiment, the deprotection step (c) can be repeated at least once, in conditions identical to or different from the 1$^{st}$ deprotection step. Such a repetition can be necessary if a monoprotected creatine fatty ester is obtained after implementing the 1$^{st}$ step (c).

Figure 4:
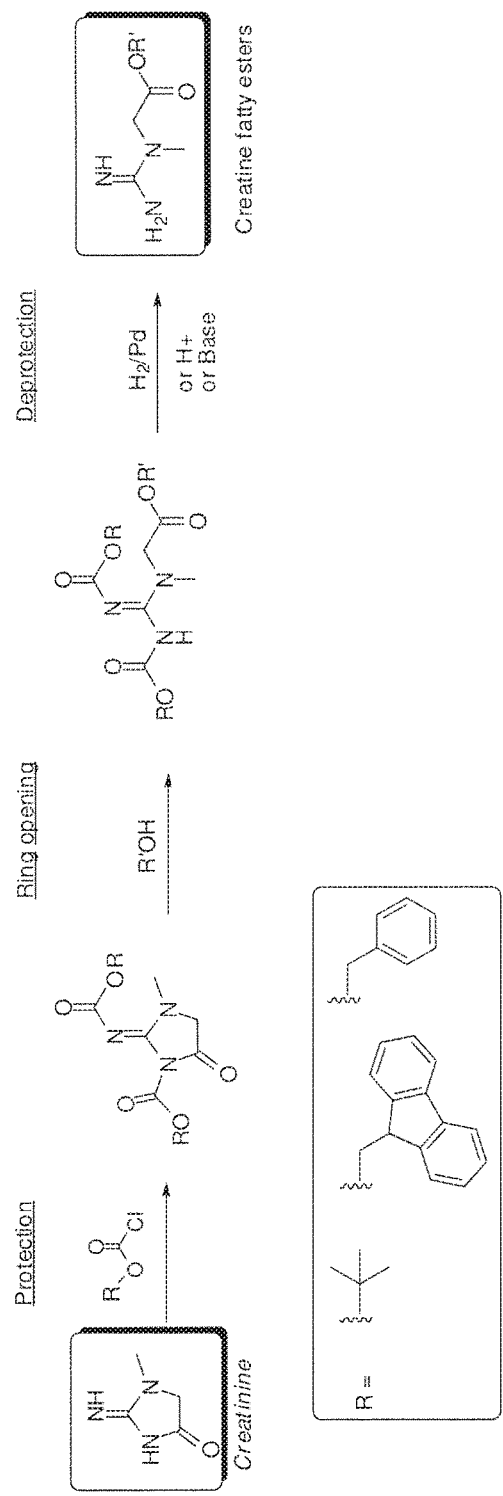

The chemical reactions carried out to prepare creatine esters in accordance with particular embodiments of the present invention are depicted in scheme 1 in FIG. 4.

The present invention also concerns compounds that can be prepared by a method according to the present invention and, more particularly, by a method into which the alcohol of formula R'—OH is glucose or substituted glucose.

In other words, the compound according to the present invention is a compound of formula (III), (IV) or (V):

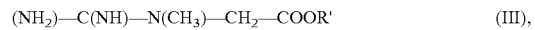

(NH$_2$)—C(NH)—N(CH$_3$)—CH$_2$—COOR'    (III),

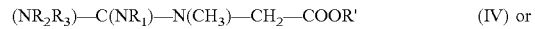

(NR$_2$R$_3$)—C(NR$_1$)—N(CH$_3$)—CH$_2$—COOR'    (IV) or

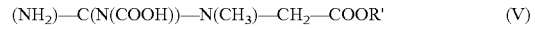

(NH$_2$)—C(N(COOH))—N(CH$_3$)—CH$_2$—COOR'    (V)

in which:

the radicals R$_1$, R$_2$ and R$_3$, identical or different, represent an hydrogen atom or a carboxylic acid group and at least one among the radicals R$_1$, R$_2$ and R$_3$ is a carboxylic acid group.

the radical R' is a glucosyl radical optionally substituted, or a salt thereof.

All the different embodiments disclosed for radicals R$_1$, R$_2$, R$_3$ and R' apply to the compound according to the present invention.

In the context of the invention, "salt" refers to acid addition salts and base addition salts. Such salts can be formed by conventional means, for example by reaction of a form of free acid or a form of free base of a compound of the invention with one or several equivalents of an appropriate acid or base, optionally in a solvent, or in a medium in which the salt is insoluble, then by extracting said solvent, or said medium, by using conventional techniques (for example in vacuum or by freeze drying). The salts can also be prepared by replacing a counter-ion of a compound of the invention in the form of a salt with another counter-ion, for example by using an appropriate ion-exchange resin.

Especially in the purpose of being administered to a human or animal body, the salts of compounds according to the invention are advantageously pharmaceutically acceptable salts.

In particular, when the compounds according to the invention are in the form of a salt, the latter being a salt of an alkali metal, in particular sodium or potassium salt, or salt of alkaline earth metal, in particular magnesium or calcium, or even a salt with an organic amide, more particularly with an amino acid such as arginine or lysine.

When the compounds according to the invention which have an amine function are in the form of a salt of this amine, the salt is a salt of inorganic acid such as, for example, hydrochloric acid, sulfuric acid, or hydrobromic acid, or in the form of an organic salt, such as, for example, acetic acid, formic acid, triflic acid, tartatic acid, oxalic acid, citric acid, trifluoroacetic acid, or methanesulfonic acid.

Moreover, the present invention concerns a composition comprising at least one compound according to the invention such as previously disclosed, in an acceptable vehicle. The vehicle will depend on the composition use and the one skilled in the art will be able the most appropriate vehicle without inventive effort.

As already explained, creatine can be used as supplement to enforce organism, increase muscle mass and enhance muscle performance. Indeed, creatine supplementation can result in positive physiological effect on muscles such as, for example, skeletal or cardiac muscles. As a consequence, the composition according to the present invention can be a food additive or a nutritional supplement. The composition according to the present invention can be useful for animals or for humans such as, for example, sports(wo)men, aged people, children, teenagers or vegetarian people.

Additional information on such use can be found in [10-11].

The present invention additionally relates to a pharmaceutical, diagnostic or imaging composition comprising at least one compound according to the invention such as previously disclosed, in an acceptable pharmaceutical vehicle.

In the context of the present invention, "acceptable pharmaceutical vehicle" refers to one or several conventional pharmaceutical additives, excipients, buffers, thinners, and/or auxiliary agents known by one having ordinary skill in the art.

The creatine fatty esters and derivatives thereof according to the present invention provide a new remediation for brain creatine deficiency transporter disease treatment. Moreover, some other pathologies can be explored under the light of these promising preliminary results.

Also disclosed is the use of such derivates able to cross the BBB in vitro and in vivo without the involvement of Solute Large Carrier Transporter (SLC6A8). So that creatine normally excluded by the BBB in patients with creatine deficiency transporter may be produced after clivage of creatine fatty esters within the brain endothelial cells and released in the brain parenchyma. Also is disclosed the potential vectorization of the creatine fatty esters which are potentially usable in vivo.

Thus, the compounds and compositions according to the present invention can be used in medicine and notably in therapeutical medicine, in medical diagnosis and in medical imaging such as by Positron Emission Tomography (PET). Indeed, the fact that the creatine part and/or the fatty ester part of the creatine fatty ester or of the derivative thereof can present radioisotope(s) as previously disclosed can be useful in diagnosis and in imaging. For example, the glucosyl radical present in the compound according to the present invention can be substituted by at least one radioisotope such $^{18}$F for use in medical imaging and more particularly in PET.

The compounds and medical compositions according to the present invention can be used for the treatment or the prevention of at least one disease, disorder or condition selected in the group consisting of Parkinson's disease, Huntington's disease, a neuromuscular disorder, hypoxia, an ischemic brain disease such as stroke, an heart disease, a muscular dystrophy, a skin disorders and inflammation.

The compounds and medical compositions according to the present invention can be used for the treatment of the brain creatine deficiency transporter disease.

In other words, the present invention concerns a method for treating or preventing at least one disease, disorder or condition selected in the group consisting of Parkinson's disease, Huntington's disease, a neuromuscular disorder, hypoxia, an ischemic brain disease such as stroke, an heart disease, a muscular dystrophy, a skin disorders and inflammation, consisting in administering to a subject in need, a therapeutical amount of a compound according to the invention or of a composition according to the invention.

The present invention also concerns a method for treating the brain creatine deficiency transporter disease, consisting in administering to a subject in need, a therapeutical amount of a compound according to the invention or of a composition according to the invention.

Additional information on such treatment methods can be found in [1-4].

Other characteristics and advantages of the present invention will additionally be apparent to the one skilled in the art on reading the examples below, which are given as an illustration and not a limitation, with reference to the attached figures.

SHORT DESCRIPTION OF THE DRAWINGS

Figure 2:
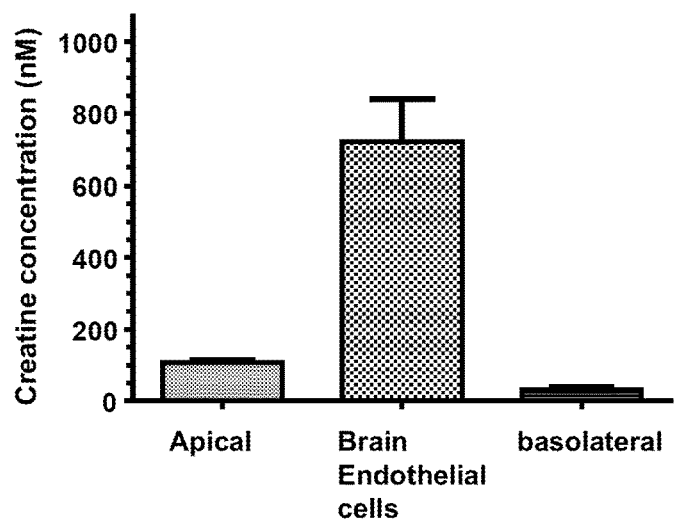
Figure 3:
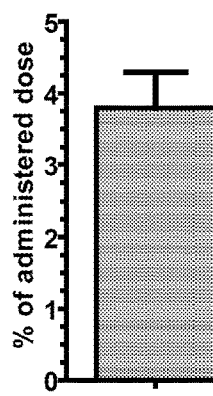
Figure 3:
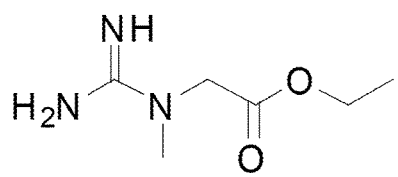
Figure 5:
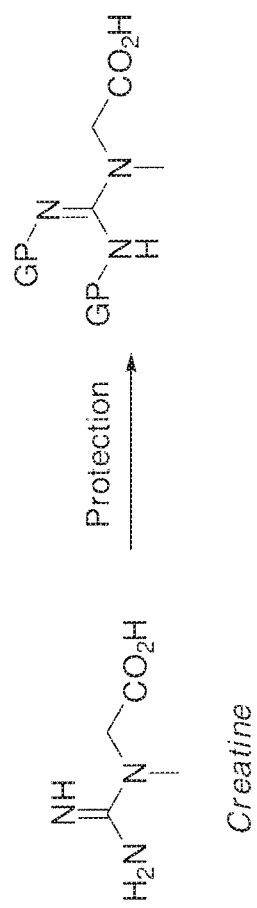
Figure 6:
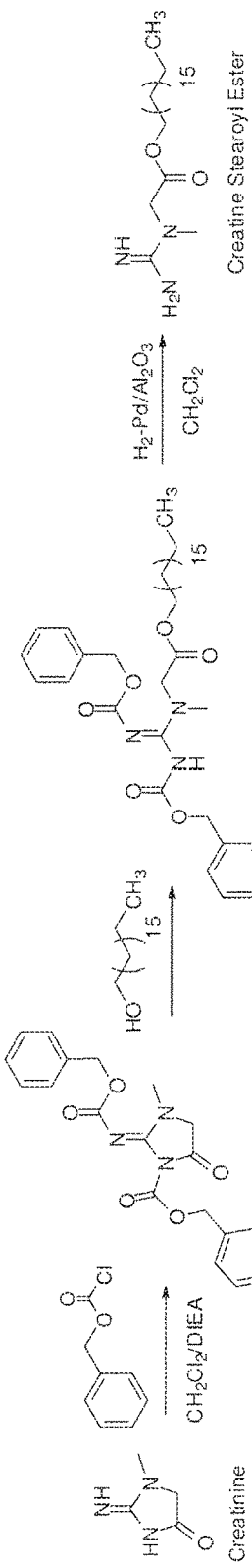
Figure 7:
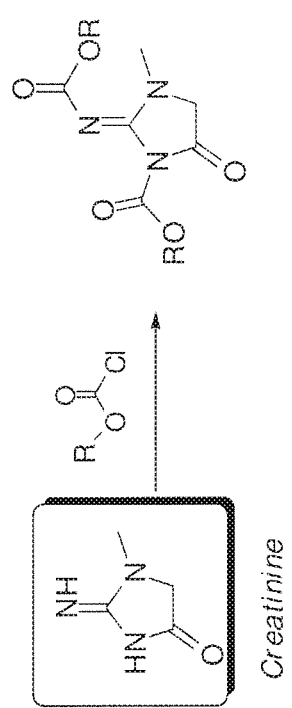

FIG. 1 presents the translocation of creatine fatty ester C18 through the BBB.
FIG. 2 presents the conversion of C18 into creatine.
FIG. 3 presents the translocation of creatine fatty ester C2 through the BBB.
FIG. 4 presents scheme 1 depicting the preparation of creatine esters.
FIG. 5 presents scheme 2 depicting the protection of creatine.
FIG. 6 presents scheme 3 depicting the synthetic sequences of a creatine stearoyl ester preparation.
FIG. 7 presents scheme 4 depicting the protection of creatinine.

DETAILED DISCUSSION OF PARTICULAR EMBODIMENTS

All the reagents are purchased from Aldrich (Steinheim, Germany). TLC was performed on Merck F 254 plates using specified solvent system. Analytical and preparative LC/MS were performed on Waters Autopurify System (SCBM). Biological evaluation of targets was performed on yyy (SPI). $^1$H and $^{13}$C NMR spectra were recorded at 400 MHz on a Bruker spectrometer.

I. Comparative Preliminary Results.
I.1. Direct Synthesis of Esters from Creatine.

The inventors tried to prepare creatine stearoyl ester using the proceedings disclosed in [7-8]. The results are presented in Table 1:

TABLE 1

| Substrate (1 mM) | Reagents | Conditions | Yield |
| --- | --- | --- | --- |
| Creatine, hydrate | Stearyl alcohol 10 eq SOCl$_2$ 3 eq | 40° C., overnight | 0% |
| Creatine, hydrate | KOH Stearyl alcohol 10 eq SOCl$_2$ 3 eq | "in situ" acyl chloride production Potassium salt of creatine Reflux 1 h | 0% |

TABLE 1-continued

| Substrate (1 mM) | Reagents | Conditions | Yield |
|---|---|---|---|
| Creatine anhydrous | Stearyl alcohol 10 eq SOCl$_2$ 3 eq | Sealed tube 80° C., 6 h | 0.1% Purified by LC/MS |
| Creatine anhydrous | Stearyl alcohol 10 eq SOCl$_2$ 3 eq | Microwave 160° C. 20 min | 0% Production of creatine acyl chloride |
| Creatine anhydrous | Stearyl alcohol 10 eq CH$_3$SO$_3$H 3 eq | 130° C. 2 h 30 | 0% |
| Creatine anhydrous | Ethanol, SOCl$_2$ | Reflux 60° C. 1 h RT 72 h | 50% crystallized |

I.2. Protection of Creatine.

The inventors tried to prepare creatine fatty esters by using protected creatine. Two protective groups (PG) were developed on creatine (see Table 2) according to [12-13] (see scheme 2 in FIG. 5).

TABLE 2 protection of creatine

| Protective Reagent | Stoech. | Conditions (RT) | Base | Stoech. | Yield |
|---|---|---|---|---|---|
| FmocCl | 3 eq | DCM | DIEPA | 3 eq | 5% |
| FmocCl | 1 eq | DCM | TMSCl/DIEPA | 4 eq/3 eq | 11% |
| Z$_2$O | 4 eq | Dioxane/Water | NaOH | 1 eq | 0% |
| ZCl | 3 eq | DCM | DIEPA | 3 eq | 33% |

With creatine, only the monoprotected derivative was produced. Unfortunately this compound was not reactive for the following step of the synthesis. Moreover, the inventors isolated a new compound not useful obtained by addition of the chloroacetyle on the methylene.

In addition, synthesis with the FMOC group led to diprotected creatinine after self cyclization in the reaction media.

I.3. Synthesis of Esters from Monoprotected Creatine.

The protocols and yields are summarized in Table 3.

TABLE 3

| Substrate | Reagents | Yield |
|---|---|---|
| (Z)creatine | DMF/DCC/DMAP | 0% |
| (Z)creatine | THF/TEA/trichlorobenzoylchloride | 0% |
| (Z)creatine | Stearyl alcohol/ 4-pyrrolidinopyridine | 1.3% |
| (Z)creatine-TriCl benzoyle | "in situ" production Stearyl alcohol/NaH/THF | 0% |

Even with the activation of the acid function of creatine by trichlorobenzoyl chloride on protected creatine, only very poor yields were obtained.

II. Synthesis of Creatine Stearoyl Ester According to the Present Invention

II.1. General Procedure.

This synthesis is carried out by opening the ring of di-protected creatinine, (Z2)-creatinine, by stearoyl alcohol followed by deprotection under hydrogen/Pd. Hereinafter, scheme 3 in FIG. 6 shows the synthetic sequences of creatine stearoyl ester preparation.

A. (Z$_2$)-Creatinine.

Benzoylchloroformate (4.2 ml-3 eq) were added to a solution of diisopropyl ethylamine (5.2 ml-3 eq) with creatinine (1.124 g-1 eq) in 100 ml of anhydrous dichloromethane under nitrogen. The benzylchloroformate is added dropwise in an ice bath. The mixture is allowed to react with stirring 30 min in the ice bath and overnight at room temperature.

The reaction is controlled by CCM (Silica, Heptane/Ethyl Acetate) and LC/MS. The reaction medium is extracted by addition of dichloromethane and water. The dichloromethane phase is washed 3 times with water and dried by magnesium sulphate.

The dichloromethane solution is concentrated by evaporation under vacuum and allowed to crystallize. 3.25 g of crude (Z$_2$)-creatinine are obtained (87%). The (Z$_2$)-creatinine can be purified on silica gel (Heptane/Ethyl Acetate gradient) for the determination of structure. The crude product is used to perform the esterification step.

B. (Z$_2$)—Creatine Stearoyl Ester.

Stearoyl alcool (0.5 g-2 eq) is allowed to react with 1 eq of crude (Z$_2$)-creatinine in a tube heated to 80° C. during 5 h. The reaction is monitored by CCM (Silica, Heptane/Ethyl Acetate) and LC/MS.

The crude (Z$_2$)-creatine stearoyl ester is purified on silica gel (Heptane/Ethyl Acetate gradient) to yield 286 mg of pure (Z$_2$)-creatine stearoyl ester with a 50% yield.

C. Creatine Stearoyl Ester.

Pure (Z$_2$)-creatine stearoyl ester (140 mg) is dissolved in anhydrous dichloromethane/methanol solution (6 ml/12 ml) under nitrogen. Pd/Al$_2$O$_3$ 5% (20 mg) is added. The reaction mixture is degassed under vacuum, frozen to be purged and the vacuum is broken by hydrogen. The purge with hydrogen is done three times. Then the medium is allowed to reach room temperature and react under vigorous stirring.

The reaction is monitored by CCM (Silica, Heptane/Ethyl Acetate) and LC/MS. When the reaction is complete, generally after 3 h, filtration on 0.5 μm filter gives creatine stearoyl ester solution.

The creatine stearoyl ester solution is evaporated under vacuum to yield 75 mg (quantitative yield).

II.2. Variants of the Method According to the Present Invention.

A. Protection of Creatinine.

TABLE 4

| Protective Reagent | Stoech. | Conditions | Base | Stoech. | Yield |
|---|---|---|---|---|---|
| Boc$_2$O | 5 eq | RT, Dioxane/Water | NaOH | 1 eq | 0.6% |
| Boc$_2$O | 6 eq | RT, DCM | DIEPA | 6 eq | 43% |
| FmocCl | 1.5 eq | RT, DCM | DIEPA | 1.5 eq | 28% |
| ZCl | 3 eq | RT, DCM | DIEPA | 3 eq | 87% |

Different protective reagents were tested in order to prepare protected creatinine (see scheme 4 in FIG. 7). Results are presented in Table 4.

Reaction of creatinine with Boc$_2$O presented very poor yield under aqueous conditions and reaction with Boc$_2$O under anhydrous conditions led to a new and unuseful compound with 3 Boc functions by addition of the Boc group on the methylene with a 43% isolated yield.

Fortunately, the reaction with the benzoyl chloroformate (ZCl) yielded 87% of diprotected creatinine used as a "crude" product after crystallisation in hexane.

B. Nucleophilic Addition of Alcohols on Diprotected Creatinine.

Different molecules bearing a alcohol group were tested for nucleophilic addition on diprotected creatinine. Results are presented in Table 5.

TABLE 5

| R' | Stoech. | Conditions | Yield |
|---|---|---|---|
| C1 | as solvent | RT 2 h | 92% |
| C2 | as solvent | 80° C. 4 h | 72% |
| iPrOH | 4 eq | 80° C. 4 h | 5.5% |
| C4 | 10 eq | 60° C. 4 h | 60% |
| C8 | 4 eq | 80° C. 4 h | 40% |
| Octanol-2 | 4 eq | 80° C. 4 h | 5% |
| C9 | 8 eq | 80° C. 5 h | 25% |
| C12 | 8 eq | 80° C. 7 h | 47% |
| C16 | 6 eq | 80° C. 7 h | 55% |
| C18 | 1.5 eq | 80° C. 16 h | 25% |
| C18 rad | 10 eq | 80° C. 5 h | 28% (HPLC) |
| C18 ins | 4 eq | 80° C. 5 h | 20% |
| Glucose | 1 eq | 80° C. 3 h 30 | 0.5% |
| Z3,OMe Glu C6—OH | 3.25 eq | 80° C. 5 h | 21% |

In Table 5, "C18 rad" means $^{14}C$ labelled compound, "C18 ins" a C18 aliphatic chain presenting insaturation(s) and "Z3,OMe Glu C6-OH" means a glucose in which 3 of the 4 alcohol groups borne by the carbon atoms 1, 2, 3 and 4 are protected, while the alcohol group borne by the carbon atom 6 is free and reacts during the ring opening step in the method according to the present invention.

Nucleophilic addition of alcohols occurs spontaneously in methanol at room temperature using the alcohol as solvent. The crude diprotected showed a better reactivity probably because acidic impurity catalyses the addition.

Increasing the length of the aliphatic chain needed to react with heating up to 80° C. The reaction time was about 3 h. Increasing the reaction time might degrade the desired compound to provide by-compounds as compounds obtained by deprotection of one protective group and transesterification by excess alcohol.

Finally, the inventors obtained 45% yields for addition of aliphatic alcohols with chain length comprised between 8 and 18 carbons.

C. Deprotection of ($Z_2$) Creatine Fatty Esters.

The deprotection of the Z groups leads to the recovery of the guanidine function, well-known for its very polar character.

Palladium over alumina was preferred to palladium over charcoal because the recovery of the desired product needs steps of washing the catalyst by less amounts of methanol.

Creatinine was systematically obtained as by product because of the propensity for cyclization of our derivatives. Creatinine is easily eliminated on reversed phase column. The deprotection of short aliphatic chain was unsuccessful because the formation of creatinine by self-cyclization was complete and no creatine ester could be obtained.

Results on the deprotection are presented in Table 6.

TABLE 6

| R' | Reactants | Conditions | Yield |
|---|---|---|---|
| C1 | TMSI, CH$_3$CN | 50° C., 30 min 40 mg/ml | Quantitative, HPLC yield |
| C1 | MeOH Pd/C 5% | PA, 1 h RT 40 mg/ml | 0% (creatinine) |
| C1 | DCE Pd/C 5% | PA, 4 h RT 40 mg/ml | 0% (creatinine) |

TABLE 6-continued

| R' | Reactants | Conditions | Yield |
|---|---|---|---|
| C4 | DCM Pd/C 5% | PA, 4 h RT 20 mg/ml | 7% (isolated by LC/MS) |
| C8 | CH$_3$CN Pd/Al$_2$O$_3$ 5% | PA, 4 h RT 1 mg/ml | 0% (mono) |
| C8 | DCM/MeOH (1/1) Pd/Al$_2$O$_3$ 5% | PA, 3 h RT 10 mg/ml | 100% (+44) |
| C8 | ACN/MeOH (1/1) Pd/Al$_2$O$_3$ 5% | PA, 4 h RT 10 mg/ml | 13% |
| C9 | DCE Pd/C 5% | PA, 3 h RT 10 mg/ml | 50% |
| C12 | CH3CN Pd/Al$_2$O$_3$ 5% | PA, 4 h RT 1 mg/ml | 0% (mono) |
| C12 | DCM/MeOH (1/4) Pd/Al$_2$O$_3$ 5% | PA, 4 h RT 10 mg/ml | 100% (+44) |
| C12 | DCM/MeOH (1/2) Pd/Al$_2$O$_3$ 5% | PA, 4 h RT 10 mg/ml | 100% (+44) |
| C16 | CH3CN Pd/Al$_2$O$_3$ 5% | PA, 3 h RT 4 mg/ml | 0% (mono) |
| C16 | DCM/MeOH (1/1) Pd/Al$_2$O$_3$ 5% | PA, RT 10 mg/ml | 100% |
| C18 | DCM/MeOH (1/2) Pd/Al$_2$O$_3$ 5% | PA, 3 h RT 8 mg/ml | 90% |
| C18 rad | DCM/MeOH (1/1) Pd/Al$_2$O$_3$ 5% | PA, 3 h RT 2 mg/ml | 65% |
| C18 ins | DCE Pd/C 5% | PA, 2 h RT 20 mg/ml | 0% (saturated analogue) |
| Glucose | DCM/MeOH (1/1) Pd/Al$_2$O$_3$ 5% | PA, 3 h RT 3 mg/ml | Molecular pic availalble |

Depending on the solvent used and the ratio of DCM/methanol or acetonitrile, the inventors produced the carbonated form of the creatine fatty ester (+44) isolated by LC/MS preparative chromatography.

The deprotection of unsaturated compounds (C18 ins) gave the saturated analogues. The method with TMSI/CH$_3$CN must be used for these compounds.

In Table 6, "0% (mono)" means that monoprotected creatine fatty ester was obtained and that additional deprotection step was necessary to prepare the deprotected form.

Finally the prepared compounds were not or poorly soluble in water or biological media and not or poorly stable in organic solution. They had to be conserved on a solid form and proceeded to the biological protocol just before their use.

That is the reason why the inventors decided to develop more hydrophilic esters by reaction with protected glucose. In such compounds, the glucose moiety acts as a ligand to favour the transport of the creatine derivatives in particular through the BBB.

III. Translocation of Creatine Fatty Esters Across the In-Vitro Cell-Based BBB Model.

The in-vitro cell-based BBB model which is used to assess the permeability of fatty esters consists in a coculture of glial cells and brain endothelial cells.

A transport buffer (150 mM NaCl, 5.2 mM KCl, 2.2 mM CaCl$_2$, 0.2 mM MgCl$_2$, 6 mM NaHCO$_3$, 2.8 mM glucose and 5 mM Hepes) is added: 1500 μl to the basolateral chamber (which represents the cerebral parenchyma) and 500 μl to the apical chamber (which represents the blood).

The fatty esters are introduced in the apical compartment. After 60 min, aliquots are removed from the apical and basolateral chambers for drug-concentration determination. The percentage of drug from the initial dosage that crossed BBB is calculated as follows: $P\ (\%) = [(Bf \times 1500)/(A0 \times 500)] \times 100$ where Bf is the amount of tested compounds in the basolateral compartment at the end point. A0 is the initial amount in the apical compartment at time point 0.

After 60 min of incubation with creatine fatty esters, the inventors noticed that fatty esters C18 but not C2 presented a good permeability through the blood brain barrier.

Indeed, in the case of creatine fatty ester C18, intracellular level of creatine stearoyl ester increased within brain endothelial cells after incubation of cells with this compound (FIG. 1). Notably, this tremendous increase in creatine stearoyl ester strikingly coincided with the appearance of creatine content (about 700 nM) within brain endothelial cells as well as in the basal compartment (about 31 nM) (FIG. 2), suggesting the potential interaction of yielded creatine with cells (e.g. neuronal cells) of brain parenchyma.

In the case of creatine fatty ester C2, the inventors found no translocation of this compound within brain endothelial cells or in the basal compartment of the in vitro cell-based blood-brain barrier model. The inventors found no evidence of the appearance of creatine content within cells or in the brain parenchyma compartment (FIG. 3).

Taken together, the present findings report for the first time differential translocation throughout the BBB between creatine fatty esters. To sum up, the inventors bring the first evidence of the usefulness of the design molecular strategy to get creatine within brain endothelial cells and brain parenchyma compartment after administration of creatine fatty esters. Creatine fatty esters can thus represent the promising candidates for the development of new drugs useful in the treatment of creatine deficiency transporter.

REFERENCES

[1] International application WO 02/22135 in the name of Board of Regents of the University of Nebraska and published on Mar. 21, 2002.
[2] Patent application US 2002/0049253 in the name of Kaddurah-Daouk and published on Apr. 25, 2002.
[3] Patent application US 2003/0212130 in the name of Miller et al. and published on Nov. 13, 2003.
[4] U.S. Pat. No. 6,413,552 in the name of Stoll and published on Jul. 2, 2002.
[5] Article of Edgar and Shiver, 1925, "The equilibrium between creatine and creatinine in aqueous solution. The effects of hydrogen ion", J. Amer. Chem. Soc., vol. 47, pages 1179-1188.
[6] Patent application CN 1616420 in the name of XinMao Dacron Chemical General and published on May 18, 2005.
[7] Patent application US 2005/0049428 in the name of Vennerstrom and published on Mar. 3, 2005.
[8] Patent application CN 1900056 in the name of Tiangcheng Pharmaceutical Co. Lt. and published on Jan. 24, 2007.
[9] International application WO 2008/101309 in the name of Multi Formulations Ltd. and published on Aug. 28, 2008.
[10] Patent application US 2011/0269986 in the name of Burov et al. and published on Nov. 3, 2011.
[11] Patent application US 2008/0200705 in the name of Chaudhuri et al. and published on Aug. 21, 2008.
[12] Article of Gers et al., 2004, "Reagents for efficient conversion of amines to protected guanidines", Synthesis, vol. 2004, pages 37-42.
[13] Article of Robles et al., 1999, "Towards nucleopeptides containing any trifunctional amino acid", Tetrahedron, vol. 55, pages 13251-13261.

The invention claimed is:

1. A method for preparing a creatine fatty ester or derivative thereof comprising:
at least one step including reacting a diprotected creatinine with a molecule bearing at least one alcohol functional group and of formula (I):

$$R'\text{---}OH \qquad (I)$$

in which R' is a hydrocarbon radical containing at least 4 carbon atoms,
wherein the diprotected creatinine includes two protecting groups each replacing a hydrogen atom substituent of a nitrogen atom of the diprotected creatinine, the two protecting groups being identical or different,
wherein the creatine fatty ester derivative has a carboxylic acid group (—COOH) replacing at least one hydrogen atom of the methylguanidinyl group of the creatine fatty ester, and
wherein the creatine fatty ester derivative is obtained after a partial deprotection of a diprotected creatinine, the protecting groups of which are formula —C(O)—OR$_4$ with R$_4$ being a hydrocarbon group.

2. The method according to claim 1, wherein the radical R' is chosen from the group consisting of an alkyl radical with 4 to 30 carbon atoms, an alkenyl radical with 4 to 30 carbon atoms, and an aryl radical with 6 to 30 carbon atoms.

3. The method according to claim 1, wherein the radical R' is of the following formula (VIII):

$$\text{---}CH_2\text{---}R'_1 \qquad (VIII)$$

in which R'$_1$ is a hydrocarbon radical containing at least 3 carbon atoms.

4. The method according to claim 1, wherein the radical R' is a glucosyl radical optionally substituted.

5. The method according to claim 1, wherein said method comprises the following successive steps:
a) reacting creatinine with a protective agent to obtain the diprotected creatinine;
b) reacting the diprotected creatinine obtained at step (a) with a molecule bearing at least one alcohol functional group and of formula (I) to obtain a diprotected creatine fatty ester; and
c) deprotecting the diprotected creatine fatty ester obtained at step (b), in order to obtain said creatine fatty ester or derivative thereof.

6. The method according to claim 5, wherein said protective agent is of formula (XII):

$$Cl\text{---}C(O)\text{---}OR_4 \qquad (XII)$$

in which the radical R$_4$ is a hydrocarbon group.

7. The method according to claim 5, wherein a solvent in a solution containing the creatinine and the protective agent implemented at step (a) is dichloromethane (DCM).

8. The method according to claim 5, wherein a solution containing the creatinine and the protective agent implemented at step (a) contains the Hünig's base or N,N-diisopropyl ethylamine (DIEPA).

9. The method according to claim 5, wherein, at step (b), for one equivalent of the diprotected creatinine, the amount of molecule bearing at least one alcohol functional group and of formula (I) expressed in equivalents is between 1 and 15.

10. The method according to claim 5, wherein said step (b) is carried out during 1 to 20 h.

11. The method according to claim 5, wherein said step (b) is carried out at a temperature between 60 and 100° C.

12. A compound prepared by a method according to claim 1, said compound having the formula (III), (IV) or (V):

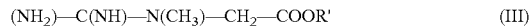 (III)

in which
radical R' is a glucosyl radical optionally substituted, or a salt thereof.

13. A composition comprising at least one compound according to claim 12, in an acceptable vehicle, wherein said composition is a food additive or a nutritional supplement.

14. A pharmaceutical, diagnostic or imaging composition comprising at least one compound according to claim 12, in an acceptable pharmaceutical vehicle.

15. A method for treating or preventing at least one disease, disorder, or condition selected from the group consisting of hypoxia and ischemic brain disease, comprising administering to a subject in need, a therapeutic amount of a compound according to claim 12.

16. A method for treating or preventing at least one disease, disorder or condition selected from the group consisting of hypoxia and ischemic brain disease, comprising administering to a subject in need, a therapeutic amount of a compound according to claim 14.

17. The method according to claim 9, wherein the amount of molecule bearing at least one alcohol functional group and of formula (I) expressed in equivalent is between 1 and 10.

18. The method according to claim 10, wherein said step (b) is carried out during 2 to 16 h.

19. The method according to claim 18, wherein said step (b) is carried out during 2 to 10 h.

20. The method according to claim 11, wherein said step (b) is carried out at a temperature between 70 and 90° C.

21. The method according to claim 20, wherein said step (b) is carried out at a temperature at around 80° C. (i.e. 80° C.±5° C.).

* * * * *